United States Patent [19]

Murray

[11] Patent Number: 4,625,722
[45] Date of Patent: Dec. 2, 1986

[54] BONE CEMENT SYSTEM AND METHOD

[76] Inventor: William M. Murray, 145 Bryce Rd., Camp Hill, Pa. 17011

[21] Appl. No.: 730,380

[22] Filed: May 3, 1985

[51] Int. Cl.$^4$ ............................................. A61B 17/00
[52] U.S. Cl. .......................... 128/92 VQ; 128/92 VP; 623/16
[58] Field of Search ................. 128/303 R, 305, 92 E, 128/92 C, 92 CA, 345, 325; 604/104, 106, 107, 8–10, 278, 213, 96; 623/16; 141/367, 312, 189

[56] References Cited

U.S. PATENT DOCUMENTS

| | | | |
|---|---|---|---|
| 3,690,323 | 9/1972 | Wortman et al. | 604/8 |
| 4,245,359 | 1/1981 | Stuhmer | 128/92 |
| 4,274,163 | 6/1981 | Malcom et al. | 128/92 |
| 4,276,659 | 7/1981 | Hardinge | 128/92 |
| 4,293,962 | 10/1981 | Fuson | 128/92 |
| 4,302,855 | 12/1981 | Swanson | 128/92 |
| 4,337,773 | 7/1982 | Raftopoulos et al. | 128/305 |
| 4,338,925 | 7/1982 | Miller | 128/92 |
| 4,344,190 | 8/1982 | Lee et al. | 128/92 |
| 4,399,814 | 8/1983 | Pratt, Jr. et al. | 128/92 |
| 4,447,915 | 5/1984 | Weber | 128/92 |
| 4,462,394 | 7/1984 | Jacobs | 128/92 E |
| 4,466,435 | 8/1984 | Murray | 128/303 |

Primary Examiner—Richard J. Apley
Assistant Examiner—H. Macey
Attorney, Agent, or Firm—Thomas Hooker

[57] ABSTRACT

A bone cement system and related methods useful in flowing liquid bone cement into a prepared long bone medullary canal prior to implanting a prothesis stem in the canal.

22 Claims, 12 Drawing Figures

BONE CEMENT SYSTEM AND METHOD

The invention relates to the components of a bone cement system for delivering liquid bone cement into a prepared long bone medullary canal and for sealing the distal end of the canal and to related methods. The components and methods are useful during implantation of a prothesis stem in the canal. The components include an improved umbrella-type delivery device, an improved pressure sealing intramedullary plug for closing the distal end of the canal and a holding and loading device for the plug.

Murray U.S. Pat. No. 4,466,435 discloses an umbrella-type delivery device for flowing liquid acrylic bone cement into a prepared long bone medullary canal before the stem is implanted in the canal. The characteristics of liquid bone cement, techniques for using the delivery device and the advantages of the umbrella-type device are discussed in the patent.

Conventionally, the distal end of the prepared medullary canal is plugged prior to filling the canal with liquid bone cement. The purpose of the plug is to limit the extent of the canal which is filled with cement. The cement is pressurized as it is flowed into the canal and also during insertion of the prothesis stem into the filled canal. The plug must effectively seal the canal to maintain the pressure of the liquid cement and prevent the cement from flowing distally past the plug.

Three kinds of plugs are presently used to seal the distal end of the femoral canal: an acrylic cement plug, a molded plastic insert plug and a plug fashioned from the live bone.

The acrylic cement plug is a mass of liquid acrylic cement introduced into the distal end of the prepared canal and maintained in place until it hardens. The plastic plug, typically molded from polyethylene, is press-fitted in place. The bone plug is fashioned from a portion of compatible bone, preferably oversized with regard to the canal end, and is then moved through the canal into the desired location.

A number of problems are associated with the conventional plugs. The cement required for the acrylic plug must be mixed and then introduced while liquid into the distal end of the canal. The canal may not subsequently be filled with liquid bone cement until sufficient time has passed for the plug cement to harden in place and close the end of the canal. A bone plug must be sized and then fitted in place. Both these of procedures take considerable operating room time. Also, it is difficult to assure that the desired close fit between a bone plug and the surrounding bone is achieved. Pressure blow-out or dislodgement of acrylic and bone plugs does occur.

Use of the acrylic plug runs the real risk that withdraw of the cement delivery nozzle following filling of the canal with liquid cement can draw the cement and plug proximally with the nozzle, thereby breaking the plug-canal seal and reducing the length of the filled canal available for placement of the prothesis stem.

Conventional molded plastic plugs are weakly anchored to the surrounding bone and may be dislodged when the liquid cement in the canal is pressurized during delivery, withdrawal of the nozzle or insertion of the prothesis stem.

Plastic and bone plugs cannot be used for closing the end of a medullary canal located distally of a narrow point having a cross section smaller than the cross section at the plug site. Additionally one molded plastic plug will not close all size medullary canals commonly experienced in performing a given procedure, thus requiring that an inventory of different sized molded plugs be maintained in order to assure that an appropriate size plug is available as required.

The umbrella-type delivery device of the invention is an improvement over the device disclosed in U.S. Pat. No. 4,466,435 and includes a shield with ribs and webbing for improved collapse of the shield before insertion of the device into the canal and subsequent expansion of the shield within the canal for improved pressure engagement with the canal walls. The pressure of the liquid cement flowed through the device and into the canal overcomes the frictional engagement between the shield and the canal so that the device is automatically expelled as pressurized liquid bone cement fills the canal. A specialized keeper is provided to stress the ribs for spring engagement against the walls of the canal.

The invention also includes an improved pressure-type intramedullary plug for sealing the distal end of the canal. The plug includes an expandable umbrella-type shield similar to the shield of the improved delivery device which, when collapsed, may be carried in the lead end of the delivery device for movement through the canal to the sealed distal end. The plug is released from the delivery device to permit the plug shield to expand and form a large area contact with the canal wall and thereby close the canal end. The shield of the delivery device is also released at the same time and likewise expands to engage the walls of the canal proximally of the expanded plug.

Liquid bone cement flowed through the delivery device and into the canal between the shields pressurizes the interior of the expanded plug shield and biases the exterior of the plug shield against the wall of the canal. The axial length of the contact between the plug shield and the canal wall is sufficient to prevent pressure movement of the plug distally, despite expected variations in the diameter of the canal. In this way, only a single plug will fit canals having a wide range of diameters.

The pressure of the liquid cement confined between expanded shields of the plug and delivery device retains the plug in place while automatically expelling the device proximally along the canal. The proximal surface of the device shield cleans the wall of the canal to promote the desired intimate and large area contact between the pressurized liquid cement and surrounding bone, as explained more fully in U.S. Pat. No. 4,466,435.

The medullary canal plug is preferably stored in a plug holder which confines the plug shield ribs in an expanded position greater in diameter than the anticipated maximum diameter of the canal at the distal end. Prior to plugging and filling the canal with cement the end of the delivery device collar is inserted into the holder which automatically collapses and inserts the plug into the collar for movement, while collapsed, through the canal to the distal end. The collapsed plug is easily moved past narrow points in the canal which would obstruct conventional large molded plastic or live bone plugs.

Other objects and features of the invention will become apparent as the description proceeds, especially when taken in conjunction with the accompanying drawings illustrating the invention, of which there are 4 sheets.

Improved umbrella-type delivery device or interfacer 10 includes a number of elements like those of the similar delivery device of U.S. Pat. No. 4,466,435. The description of the present device uses terminology which in some respects differs from the terminology used in describing the prior device. In the present description, old terminology will be set forth in parentheses for purposes of clarification.

Figures 1, 2, 3:
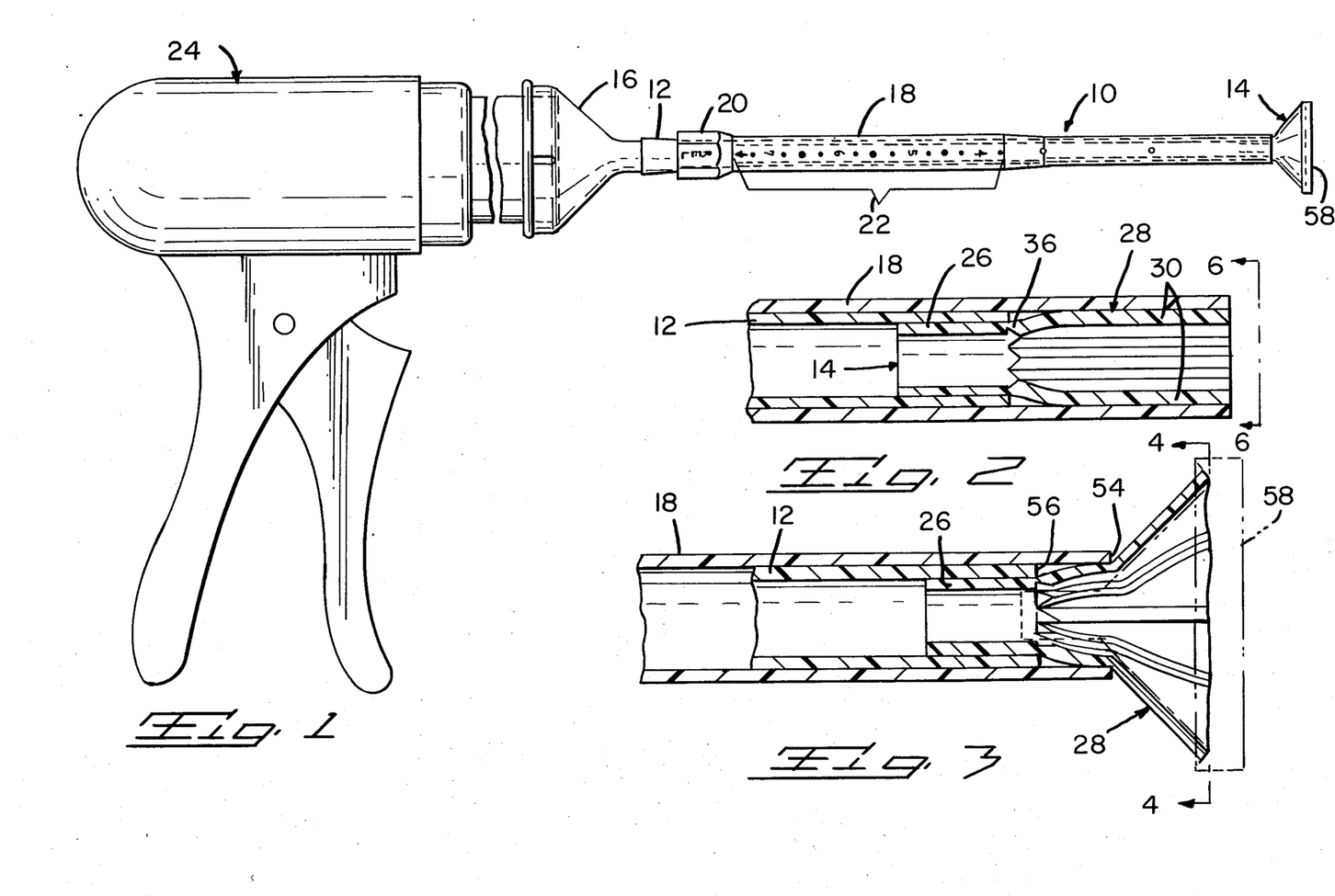
FIG. 1 is a side view illustrating a bone cement dispenser with an umbrella-type delivery device according to the invention.
FIGS. 2 and 3 are sectional views of the free end of the delivery device showing the shield in different positions.

The delivery device (nozzle) 10 includes a liquid cement delivery nozzle (tube) 12, with an expandable tip 14 on the free or distal end thereof and an enlarged cap 16 on the other or proximal end thereof as shown in FIG. 1. Cylindrical collar 18 surrounds the nozzle 12 and is slightly shorter in length than the nozzle. The collar has a sliding fit on the nozzle so that it may be moved distally and proximally on to the nozzle by gripping expanded hexagonal handle 20. Indicia 22 are spaced along the length of the collar adjacent the handle to permit the surgeon to judge the depth of insertion of the delivery device within the medullary canal.

The device cap 16 includes means for attachment to a reservoir of liquid bone cement carried by bone cement dispenser 24 which, when actuated, flows pressurized liquid bone cement from the reservoir through the cap and nozzle and outwardly of the device through tip 14.

Delivery device tip 14 is preferably molded from a plastic material and includes a cylindrical tip tube 26 and an expandable bone cement shield 28 extending from one end of the tip tube 26. The shield includes a plurality of circumferentially spaced ribs 30 extending from the end of the tip tube to the shield lip 32. Flexible plastic sheeting 34 extends between adjacent ribs 30 from the end of the tip tube to the lip so that when the shield is freely expanded the straight ribs 30 project outwardly of the tube and the sheeting is taut between the ribs. The inner ends of the ribs are joined to the tip tube by reduced cross section hinge connections 36.

Figure 4:
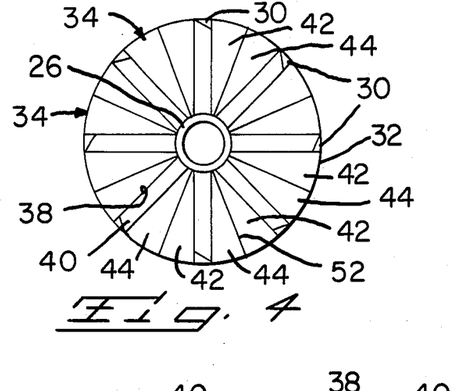
FIG. 4 is a view taken along line 4—4 of FIG. 3.
Figures 5, 7, 8:
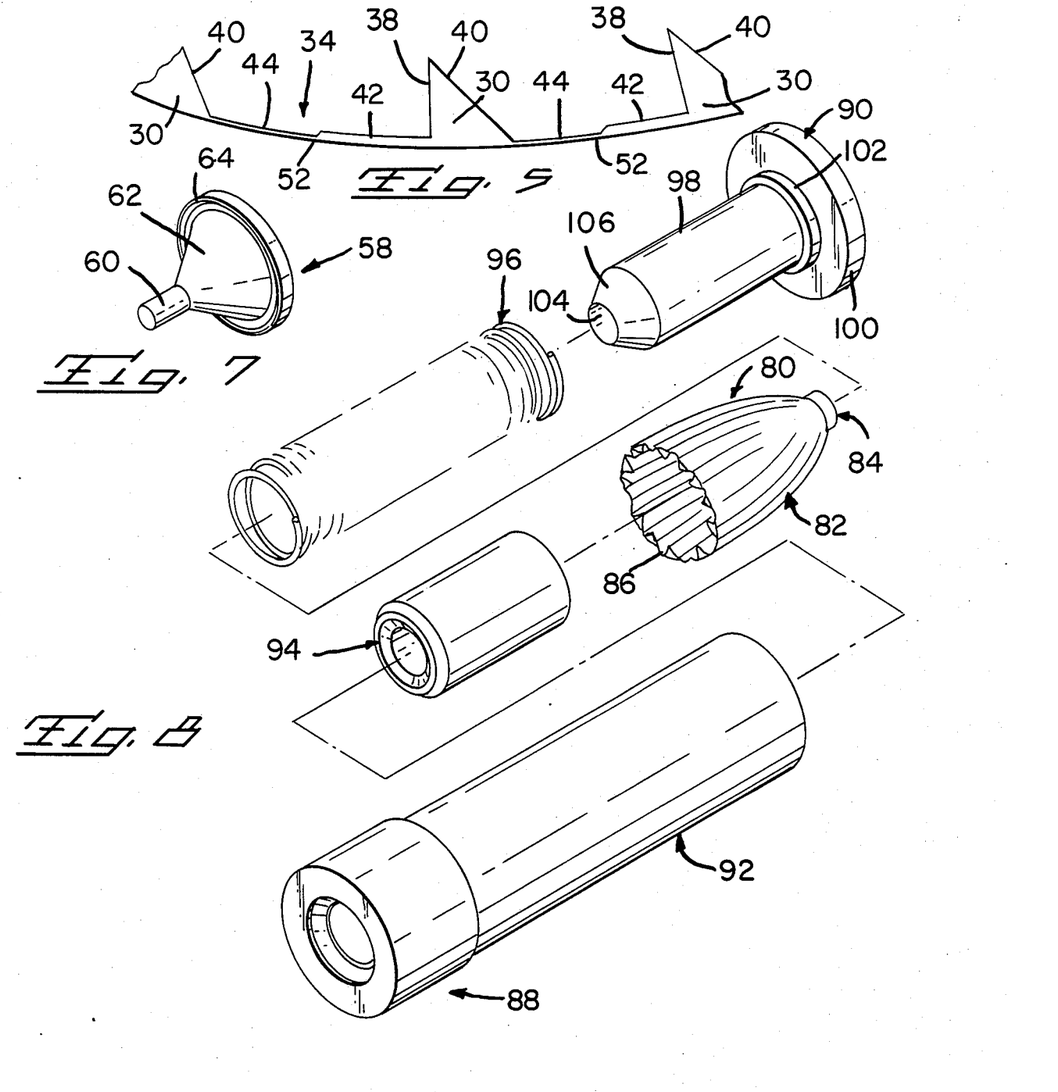
FIG. 5 is an enlarged view of the lip of the shield of FIG. 4.
FIG. 7 is a perspective view of a keeper shown in dotted lines in FIG. 3.
FIG. 8 is an exploded view of a holder for a intramedullary plug.

As illustrated in FIGS. 4 and 5, the ribs 30 are triangular in transverse cross section and each includes a side 38 on the interior of the shield lying approximately in a radial plane with all of the ribs sides 38 facing in the same circumferential direction. Each rib 30 also includes an interior side 40 facing to the opposite circumferential direction and intersecting the adjacent side 38 at an acute angle. Each sheeting portion 34 between two ribs is generally triangular in shape as illustrated in FIG. 4 and extends between the surfaces 38 and 40 of the ribs 30. The sheeting of portions 34 includes a triangular relatively thick portion 42 extending from adjacent rib surface 38 and a relatively thin sheeting portion 44 extending from the edge of portion 42 to the adjacent rib surface 40. Each of the sheeting portions 40 and 42 extends along the ribs from lip 32 to the junction between the shield and the tip tube 26 and are joined mid-way between the ribs at boundary 52.

The tip 14 is secured to the distal end of nozzle 12 by inserting the tip tube 26 within the end of the nozzle and forming a suitable permanent bond between the tip tube and nozzle.

Figure 6:
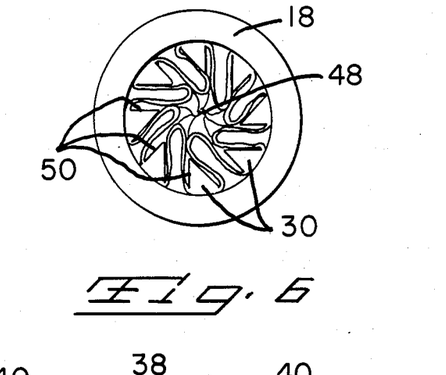
FIG. 6 is a view taken along line 6—6 of FIG. 2.

The fully expanded molded tip 14 may be passed through a suitable collapsing die which includes surfaces for forcing the ribs and triangular sections of flexible sheeting 34 inwardly to collapse the shield and fold portions 42 and 44 onto themselves and form U-shaped folded pleats 48 as shown in FIG. 6 between the collapsed and generally parallel axially extending ribs 30. When the ribs are collapsed to this position the surfaces 38 and 40 of adjacent ribs generally parallel to each other and define a series of pleat-confining slots 50 between the ribs, all of which extend in the same non-radial direction from the outer circumference of the collapsed shield. The boundary 52 between sheeting portions 42 and 44 is about equal distant between the adjacent ribs 30 so that when the sheeting 34 between the ribs is collapsed to form the pleats sheeting portions 42 form one side of the pleats adjacent surfaces 38, portions 44 form the other side of the pleats adjacent rib surfaces 40 and the portions are folded over on each other within the thinner or more flexible sheeting portions near the boundaries 52. The boundaries are at the crests of the pleats. The angled slots 50 permit efficient use of the limited available storage space such that the pleats may have a collapsed length at the shield lip greater than the interior radius of the collar. Orderly collapse of the sheeting permits a shield having a relatively large diameter when expanded to be collapsed into a relatively small diameter configuration. The collapse of each sheeting portion 34 into a like pleat 48 assures that each of the sheeting portions opens properly when the shield is expanded to form a proper pressure seal between the shield and the surrounding wall of the medullary canal.

As shown in FIG. 2, when the tip 14 is secured to the end of nozzle 12 the bone cement shield 28 may be collapsed within the extended free end of the surrounding collar 18. In practice it has been found advantageous to maintain the shield in the position of FIG. 3 during the interval prior to use for delivery of cement into a medullary canal. In FIG. 3 the collar 18 has been withdrawn from the position of FIG. 2 proximally sufficiently to position the free collar end 54 about one-third of the length of the ribs distally of the hinge connections 36 joining the ribs and the tip tube. The hinge connections are located at or beyond the free end 56 of nozzle 12. With the collar in this position a keeper 58, shown in FIG. 7, is inserted into the interior of the shield to expand the shield and bend ribs 30 outwardly about the collar end 54. See FIG. 3.

Keeper 58 is generally funnel-shaped and includes a cylindrical pilot 60, a conical shaping member or body 62 and a circumferential lip 64 at the surrounding the major end of the shaping member.

As illustrated in FIG. 3, when the keeper 58 is inserted into the interior of the bone cement shield 28 the pilot 60 extends into the tip tube and the conical shaping member 60 engages the portions of the ribs outwardly of collar end 54 and flexes them outwardly against the end, which forms a fulcrum. The pleating between the outwardly bent portions of the ribs, is at least partially unfolded. When fully inserted, the keeper lip 54 meets the ends of the ribs and protects the shield lip prior to use.

Following manufacture of the delivery device 10 a keeper 58 is inserted into the nozzle as shown in FIG. 3 so that during the storage interval prior to use ribs 30 are confined in a shallow V-shape as shown in FIG. 3. While held in this position the plastic ribs experience cold flow and tend to assume the V-shape in which they are confined. Before the delivery device is used the keeper is removed and the bone cement shield is collapsed by distal extension of the collar as in FIG. 2 and the rib ends are biased outwardly against the collar so that they will snap open after the collar is withdrawn. This assures that the shield will properly open within the canal. Further, the expanded ribs will be forced outwardly against the wall of the canal thereby improving the shield-wall seal. This feature improves the ability of the shield 28 to make an effective seal with different diameter medullary canals so that a single delivery device may be reliably used to deliver bone cement into medullary canals of different diameters encountered in performing a given procedure.

Initial collapse of the bone cement shield 28 is achieved by moving the shield through the collapsing die as described. Subsequent collapse of the shield by the collar is achieved by pushing the ribs radially inwardly. As the collar is moved distally the end 54 pushes the ribs inwardly and the relatively thin sheeting portions 44 are first folded inwardly towards the adjacent rib surface 40 while the relatively thick sheeting portions 42 resist being bent with respect to its adjacent rib 30. Further rib collapse then folds the thick sheeting portions 42 inwardly with respect to the adjacent ribs 30, thereby completing the pleats as shown in FIG. 5 and assuring that each pleat is U-shaped as described with the webbing portions 42 and 44 forming the pleat sides.

FIG. 6 illustrates that the relatively thick sheeting portions 42 resist being bent relative to their adjacent rib surfaces 40 and hold the relatively thin sheeting portions 44 closely against surfaces 40 of their adjacent ribs 40.

The bone cement shield of discharge device 10 is provided with eight ribs 30. It is contemplated that the shield may be provided with a greater number of equally spaced ribs. Such a shield would have the advantage of reducing the circumferential length of each portion of flexible sheeting between ribs. By reducing the length of the portions at the circumference of the shield the maximum length of the pleats is reduced, making storage of the pleats easier within the interior of the surrounding collar. For instance, increasing the number of ribs from 8 to 12 would markedly reduce the maximum circumferential length of each sheeting portion making it easier to fold and store the pleats within the limited interior of the collar.

The tip 14 may be molded from a polyurethane plastic possessing sufficient strength and elastomeric properties to permit the shield to be collapsed and expanded and to form the desired pressure seal with the medullary canal as described.

The delivery device 10 disclosed herein is particularly useful in flowing liquid bone cement into the interior of prepared femoral medullary canals prior to mounting a femoral prothesis within the canal. The normal diameter expected in an adult femoral medullary canal has a range of from 10 to 18 millimeters or about 0.39 to 0.71 inch. A single delivery device 10 may be used for reliably flowing cement into canals within this range.

In the device 10 the outside diameter of the tip tube is about 0.33 inch. The straight length of rib 30 is about 0.5 inch. When the shield is fully expanded the ribs diverge from the shield axis at 30 degrees and the maximum diameter of the shield at lip 32 is 1.33 inch. The relatively thin sheeting portion 44 has a thickness of about 0.006 inch and the relatively thick sheeting portion 44 has a thickness of about 0.015 inch, 2½ times the thickness of the thin sheeting. Rib surfaces 38 and 40 intersect at an angle of about 45 degrees. The fully collapsed shield shown in FIG. 2 is confined within the interior of collar 18 has an interior diameter of about 0.38 inch. The outside diameter of the distal end of the delivery device 10 is about 0.44 inch.

The keeper conical shaping member 62 has sides which diverge from its axis at an angle of 45 degrees so that when the keeper is inserted into the partially confined shield as shown at FIG. 3 the free portions of the ribs 30 are bent away from the shield axis 45 degrees in order to bend the ribs into the shallow V-shaped previously described.

FIG. 8 includes a prospective view of an intramedullary canal plug 80 useful in pressure-sealing the distal end of a medullary canal to maintain the pressure of liquid acrylic bone cement within the canal and prevent the cement from flowing distally past the plug. Plug 80 includes a bone cement shield 82 and a solid base 84 at one end of the shield. The shield 82 is similar to the delivery device shield 28 previously described and includes 12 elongate ribs extending from the base to the shield lip 86, hinge connections between the ribs and the base and differential thickness webbing portions between the ribs as in shield 28. The diameter of the base is slightly smaller than the interior diameter of the collar 18. The ribs are 0.75 inch long, 1½ times the length of ribs 30. When the plug is fully expanded the maximum diameter at the shield at lip 86 is 1.83 inch. When fully expanded, the ribs extend outwardly of the plug axis at an angle of 30 degrees. The fully expanded plug has a maximum diameter at lip 86 of 1.83 inch. The ribs of shield 82 are triangularly shaped like ribs 30 and cooperate with the differential thickness flexible sheeting between the ribs for controlled collapse of the shield with the formation of U-shaped pleats between adjacent ribs when collapsed. When fully expanded, shield 82 assumes a conical shape with the straight ribs extending 30 degrees from the plug axis. The ribs of shield 82 are longer than the ribs of shield 28 in order to assure that the plug is immovably pressure sealed to the medullary canal wall during flowing of bone cement into the canal.

The intramedullary plug base 84 is cylindrical in transverse cross section, but unlike the tip tube is solid, without a central opening. In this way, the expanded plug effectively closes off the distal end of the medullary canal.

Plug 80 may also be molded from a strong, flexible plastic material such as polyurethane. The plug is molded in an expanded, generally conical shape and then moved through a collapsing die to fold the sheeting inwardly between the ribs in the same manner as described in connection with the shield 28. The plug is then positioned within the plug holder 88 shown in FIGS. 8 and 9.

Plug holder 88 includes base 90, an elongate cover 92, collapser member 94 and spring 96. Plug holder base 90 includes a cylindrical post 98, a circular flange 100 at one end of the post with a step 102 at the junction between the flange and the cylindrical post. A shallow bore 104 is provided on the other end of post 98 for receiving and holding plug base 84. Bevel surface 106 extends from the side of post 98 inwardly to the end of bore 104.

Cylindrical cover 92 includes a cylindrical interior recess 108 opening at one end such that the cover may be fitted over the base with the open end fitted snugly around step 102 to assure the cover is maintained coaxial with the base. A beveled lead-in opening 110 is provided in the other end of the cover away from the base and has a minimum diameter less than the diameter of recess 108'.

Collapser member 94 has a close sliding fit within bore 108' and is biased toward the opening 110 by spring 96. The spring is fitted over post 98 and is confined between the step 102 and the outer circumferential end 112 of the collapser member. The collapser member includes a first circular recess 114 having a diameter approximately equal to the interior diameter of the spring 96, a minimum diameter recess 116 spaced from recess 114 and having a diameter slightly less than the interior diameter of the delivery device collar 18, a beveled shield collapse recess 118 joining recesses 114 and 116 for collapsing the shield 82 and an end recess 120 located between recess 116 and the end of the collapser member 94 away from base 90. The diameter of recess 120 is slightly greater than the exterior diameter of collar 18. The outer end of recess 120 is provided with a lead-in champer 122 which forms a continuation of bevel surface 110 when the collapser member is held against the end of the cover as shown in FIG. 9.

Figure 9:
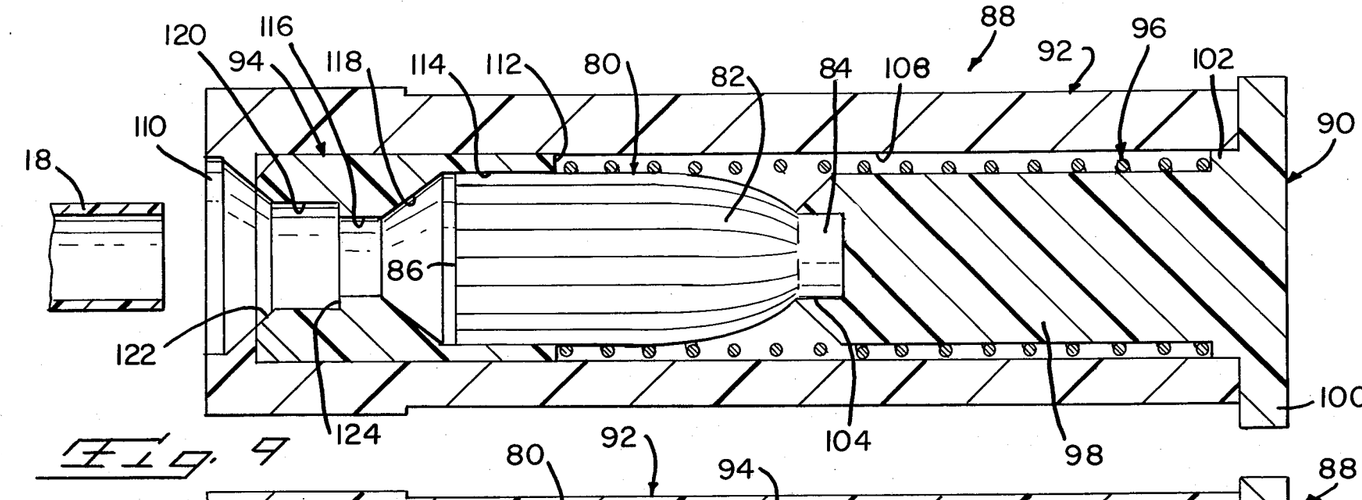
FIGS. 9 and 10 are cross sectional views of the plug holder illustrating normal retention of the intramedullary plug and insertion of the plug into the end of the delivery device.

The intramedullary plug 80 is confined within the plug holder 88 as shown in FIG. 9 with the plug base 84 fitted within bore 104 and the bone cement shield confined in a partially expanded position by the coils of spring 96 and bore 114. The ribs are molded straight so that when the plug is collapsed and confined as shown the ribs are stressed and resiliently hold the shield against the spring and bore thereby assuring that after the plug is collapsed and seated within the delivery device collar and released in the distal end of the canal the shield will snap open and the ribs will hold the shield against the canal wall for forming an immovable pressure seal. During storage of the plug within the holder the ribs tend to cold flow and assume the confined position thereby assuring that the released plug will snap open. In the case of a intramedullary plug used to close the proximal end of a femoral canal, the interior diameter of the spring and of recess 114 may be about 0.75 inch which is greater than the maximum expected diameter of the canal.

Figure 10:
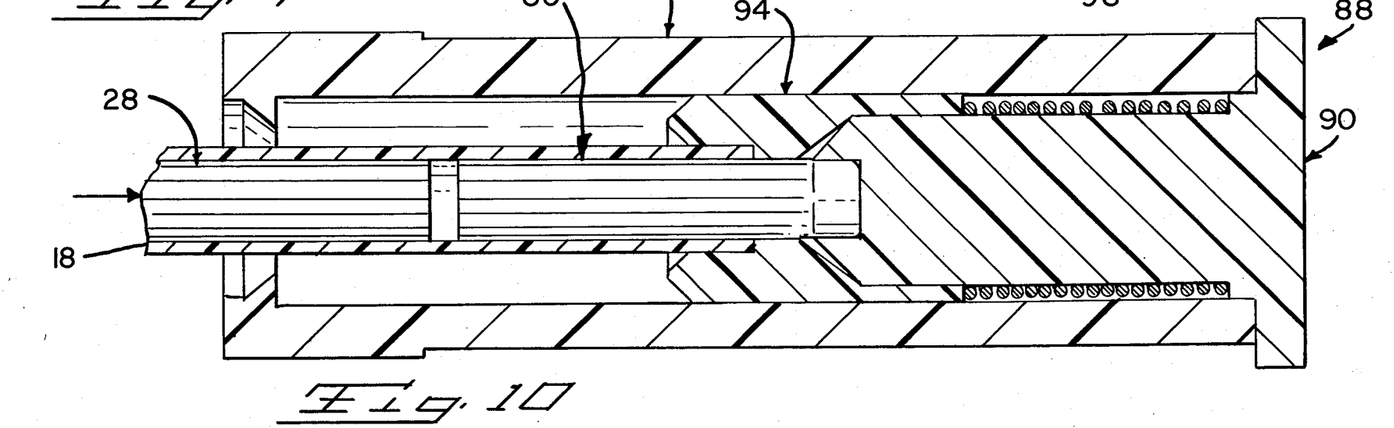
Figure 11:
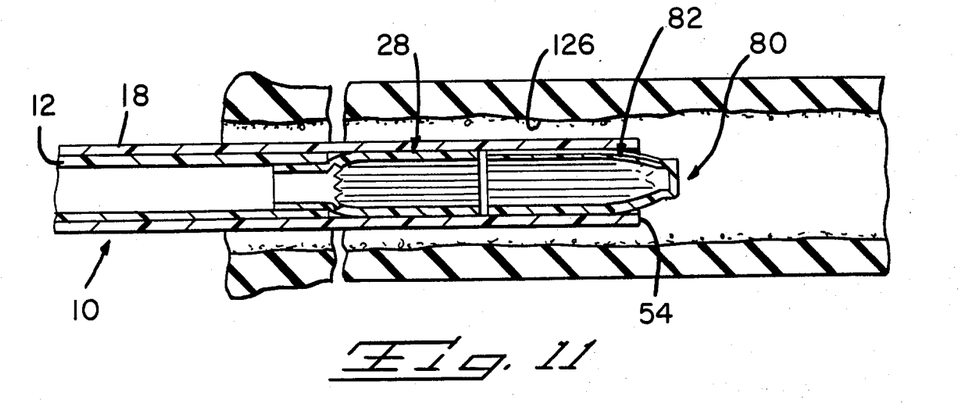
FIGS. 11 and 12 illustrate use of the plug and dispensing device in flowing liquid bone cement into a medullary canal.

The expanded intramedullary plug 80 confined in holder 88 is collapsed and loaded into the lead or distal end of delivery device collar 18 immediately after the device bone cement shield 28 has been collapsed and loaded into the collar as shown in FIG. 2. The collar is extended distally from the position of FIG. 2 so that end 54 is beyond the collapsed device bone cement shield 28 a distance sufficient to receive the collapsed plug 80. The distal end of the collar is then positioned as shown in FIG. 9 and pushed into the plug holder through lead-ins 110 and 122 until it seats on step 124 at the end of end recess 120. The diameter of adjacent recess 116 is slightly less than the interior diameter of collar 18. With the base 90 supported against movement the collar is then forced toward the base as indicated in FIG. 10 so that the collapser member 94 is moved to the right and spring 96 is compressed. With plug base 84 bottomed in bore 104 the plug is held against movement so that the lip 86 of the partially collapsed plug shield 82 is brought into contact with the shield collapse recess surface 118 and moved radially inwardly and ultimately extended into the minimum diameter recess 116. During collapse of the plug shield the relatively thick and relatively thin sheeting portions between adjacent ribs are folded together as described in connection with the collapse of the device shield 28 to form U-shaped pleats which are confined within angled recesses between adjacent ribs upon full collapse.

As the collapser member 94 moves to the right the collapsed shield is loaded within the interior of the collar adjacent the previously loaded device shield 28 as indicated in FIG. 10. Loading is completed when the collapser member 94 bottoms on the end of post 98. The loaded device 10 may then be freely withdrawn from the plug holder 88. The base and part of the collapsed plug shield may extend beyond collar end 54.

After loading of plug 80 into the distal end of the extended collar 18 the surgeon moves the distal end of device 10 into the medullary canal, using indicia 22 to determine when the device is inserted to a proper depth. The surgeon then grips handle 20 and fully pulls back the collar while holding the dispenser 24 fixed so that collar 18 is withdrawn to the position of FIG. 12. Withdrawal of the collar substantially simultaneously releases both of the plug and device bone cement shields 82 and 28 for expansion in the distal end of the canal as illustrated in FIGS. 12.

The ribs of the released bone cement shields are biased outwardly against the interior wall of the canal as illustrated. Liquid acrylic bone cement 128 is then flowed from dispenser 28 through the interior of nozzle 12 and outwardly through the tip 14 into the space 132 between the expanded bone cement shields. The pressurized cement biases the expanded shields against the canal wall 126 and may capture an air pocket 130 at the distal or base end of the plug. During initial flowing of the pressurized cement into the space 132 a limited amount of cement 134 may flow past the shields at small aperatures between the ribs. These aperatures are immediately plugged by the cement so that the pressure builds up in space 132 and forces the ribs and sheeting out against the wall 126, thereby maintaining a full pressure differential between the shields and the wall.

Figure 12:
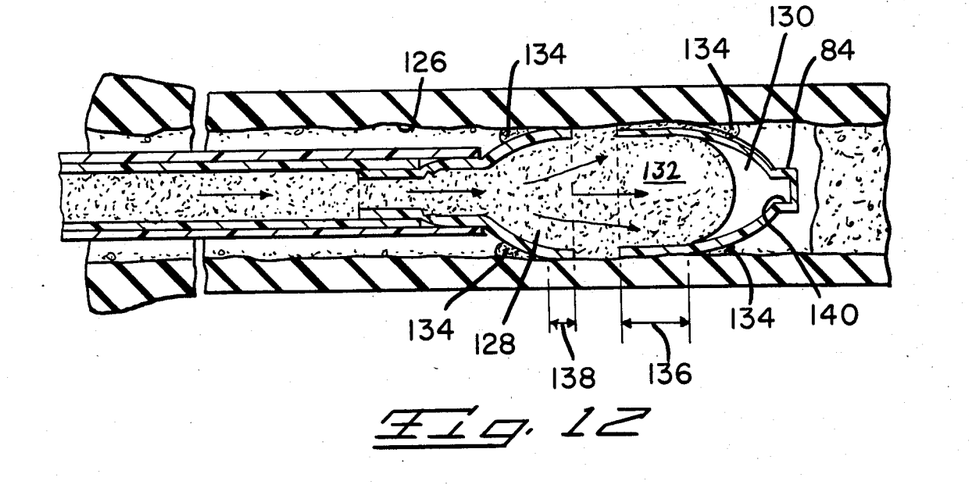

The bone cement shield 82 of plug 80 contacts the circumference of wall 126 for an axial distance indicated by 136 in FIG. 12. The bone cement shield 28 of delivery device 10 has circumferential contact with wall 126 for an axial distance indicated by 138, less than distance 136.

The pressure of the cement 128 within space 132 biases the shields against the wall 126 along a circumferential area determined by the diameter of the canal and the axial distance the shield contacts the canal.

Pressurization of the interior of a bone cement shield by liquid bone cement will exert an axial force on the shield tending to move the shield along the canal and will also force the shield against the wall of the canal and generate a frictional force resisting movement along the canal.

The axial force applied to the shield is:

$$F_{axial} = (P_c)(pi)(D_c/2)^2;$$

where $P_c$ is the pressure of the bone cement, $D_c$ is the diameter of the canal at the shield and pi as used in this and subsequent formulas, is the ratio of the circumference of a circle to its diameter.

The maximum frictional force resisting movement of the shield is:

$$F_{friction} = (L_a)(pi)(D_c)(P_c)(mu);$$

where $L_a$ is the axial length of contact between the shield and the canal wall, $D_c$ is the diameter of the canal at the shield, $P_c$ is the pressure of the cement in the shield and mu is the co-efficient friction between the shield and the wall.

The pressurized cement will not move the shield along the canal when the axial force $F_{axial}$ is less than or equal to the maximum friction force resisting movement, $F_{friction}$, or:

$$(P_c)(pi)(D_c/2)^2 \leq (L_a)(pi)(D_c)(P_c)(mu); \text{ or } D_c/L_a \leq 4 \text{ mu}$$

Conversely, in order to assure that a bone cement shield is moved along the canal by the pressure of the liquid cement flowed into the canal the axial pressure exerted on the shield, $F_{axial}$, must be greater than the maximum frictional force resisting movement between the shield and the canal wall or:

$$D_c/L_a > 4 \text{ mu}$$

It will thus be seen that for a given diameter canal a shield on the tip of a delivery device must have a short $L_{axial}$ in order for the pressurized cement to expel the device from the canal while a intramedullary plug must have a relatively long $L_{axial}$ to assure against pressure dislodgement. Expulsion or pressure retention of the bone cement shield is not dependent on the pressure of the cement.

The long ribs and sheeting between the ribs of intramedullary plug 80 assure that the end of the plug bone cement shield 82 has an annular area of pressure contact 136 with the canal wall sufficiently long to assure enough friction that the axial force exerted on the plug by the pressurized bone cement is incapable of dislodging the plug distally, independent of the pressure of the liquid bone cement. The pressurized liquid cement maintains the plug in place to seal the distal end of the canal.

The axial length of the engagement between the bone cement shield 28 of device 10 is considerably shorter than that of the intramedullary plug 80 so that, applying the formulas above, the axial force exerted on the shield 28 and the bone cement reservoir exceeds the frictional force restraining movement of the field in the canal so that the pressurized cement will force the shield, device and dispenser 24 axially proximally of the canal as pressurized liquid bone cement is flowed into the space 132 between the shields.

During the filling of the canal the surgeon actuates the dispenser 24 to maintain the pressure of the bone cement. Higher pressure may be achieved by actuating the device and manually resisting expulsion of device 10 from the canal. Movement of the bone cement shield 28 along the canal surface 126 as the canal is filled with pressurized bone cement cleans and scrapes the canal surface so that the liquid cement on the high pressure side of the shield flows into the interstices of the clean surface, as explained more fully in U.S. Pat. No. 4,466,435. After the canal is filled with cement and device 10 has been expelled a prothesis stem is implanted in the canal in a conventional manner.

An intramedullary plug 80 may be positioned in the end of a conventional bone cement nozzle without a bone cement shield using a plug holder 88. The empty end of the conventional nozzle is pushed into the holder to collapse the plug and seat it within the nozzle tip. After the nozzle is extended into the canal to position the plug at the distal end, cement is flowed through the nozzle to force the plug out into the canal, where it expands and seals the end as described.

Alternatively, an expanded plug 80 may be pushed through the canal to the distal end using an elongate insertion rod, the lead end of which is seated in recess 140 formed in the pressure side of the shield base 84. See FIG. 12. Pressurized bone cement subsequently flowed into the canal assures that the plug immovably seals the distal end of the canal.

An additional advantage of this plug is that at time of prothesis insertion into the canal the plug can be pushed further distally by the prothesis tip if it was inadvertantly placed at too shallow a depth in the femoral canal. In contrast, other commonly used plugs cannot be moved more distally without the strong possibility of dislodging them so that they no longer are anchored in the canal or without having to exert excessive and dangerous pressure to move them, or both of these problems.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim my invention is;

1. A bone cement delivery device for flowing bone cement into a long bone medullary canal including a tubular nozzle, an umbrella-type bone cement shield at the distal end of the nozzle, and means at the proximal end of the nozzle for attaching the device to a source of bone cement so that cement may be flowed from the source through the nozzle, past the shield and into the canal, the shield comprising a plurality of ribs joined to, circumferentially spaced around and extending outwardly of the distal end of the nozzle and a plurality of flexible sheeting portions each extending between adjacent ribs from the distal end of the nozzle to the shield lip, each sheeting portion including a first relatively more flexible part near one adjacent rib and a second relatively less flexible part near the other adjacent rib whereby upon collapse of the shield the first sheeting parts fold inwardly before the second sheeting parts fold inwardly.

2. A device as in claim 1 wherein each rib includes a first side on the interior of the shield lying approximately in a radial plane and facing in a first circumferential direction and a second side on the interior of the shield extending toward the first side at an acute angle and facing in the opposite circumferential direction whereby upon collapse of the shield with the ribs extending in an axial direction from the distal end of the nozzle the sides of adjacent ribs parallel each other and define like non-radial sheeting confining slots, said sheeting being folded in pleats in said slots.

3. A device as in claim 1 wherein all said first parts are on the same circumferential side of the sheeting portions so that such portions collapse in a like manner.

4. A device as in claim 3 wherein the thickness of the first sheeting part is less than the thickness of the second flexible sheeting part.

5. A device as in claim 4 wherein each flexible sheeting portion is generally triangular in shape with long sides joining the adjacent ribs and a short side forming a portion of the shield lip when the shield is expanded and the parts are generally triangular in shape, join each other at a boundary approximately midway between the adjacent ribs and extend from the distal end of the nozzle to the shield lip.

6. A device as in claim 5 wherein each rib includes a first side on the interior of the shield lying approximately in a radial plane and facing in a first circumferential direction and a second side on the interior of the shield extending toward the first side at an acute angle and facing in the opposite circumferential direction whereby upon collapse of the shield with the ribs extending in an axial direction from the distal end of the nozzle the sides of adjacent ribs parallel each other and define like non-radial sheeting confining slots, said sheeting being folded in pleats in said slots.

7. A device as in claim 6 wherein said ribs are generally triangular in cross section and the sides extend toward each other at angles of about 45 degrees.

8. A device as in claim 7 wherein the length of the ribs is about 0.5 inch, the maximum diameter of the shield at the lip when expanded is about 1.33 inch and the ribs extend away from the nozzle at about 30 degrees. When fully collapsed the outside diameter of the shield is about 0.38 inch.

9. A device as in claim 8 wherein the shield is formed from a plastic material and the relatively thick sheeting parts have a thickness of about 2½ times the thickness of the relatively thin sheeting parts.

10. A device as in claim 9 wherein the thickness of each relatively thick sheeting part is about 0.015 inch and the thickness of each relatively thin sheeting part is about 0.006 inch.

11. A device as in claim 6 including a short cylindrical tube integral with the shield and fitted within and joined to the distal end of the nozzle, the shield extending from the tube outwardly of the nozzle.

12. A device as in claim 1 including a cylindrical collar surrounding the nozzle, said collar including a distal end which may be moved distally to engage the shield ribs for collapse of the shield within the collar.

13. A device as in claim 12 wherein the distal end of the collar is located between the distal end of the nozzle and the free end of the ribs and including a conical keeper fitted within the portion of the shield extending beyond the distal end of the collar, the keeper including a conical shaped member engaging the interior of the shield ribs and bending the ribs radially outwardly against the end of the collar so that the ribs have a shallow V-shape.

14. A device as in claim 13 wherein the keeper includes a cylindrical pilot, said pilot extending into the portion of the shield located within the collar.

15. A device as in claim 13 wherein the sides of the conical shaping member diverge from the axis of device at about 45 degrees.

16. A device as in claim 12 wherein the distal end of the collar is located between the distal end of the nozzle and the free end of the ribs and including a keeper having a shaping member engaging the interior of the shield ribs extending beyond the distal end of the collar and bending the ribs radially outwardly against the end of the collar.

17. A bone cement delivery device for flowing bone cement into a long bone medullary canal including a nozzle, an umbrella-type bone cement shield at the distal end of the nozzle, and means at the proximal end of the nozzle for attaching the device to a source of bone cement so that bone cement may be flowed through the nozzle, past the shield and into the canal, the bone cement shield comprising a plurality of ribs joined to, circumferentially spaced around, and extending outwardly of the distal end of the nozzle and flexible sheeting portions extending between adjacent ribs, each rib including a first side on the interior of the shield lying approximately in a radial plane and facing in a first circumferential direction and a second side on the interior of the shield extending toward the first side at an acute angle and facing in the opposite circumferential direction whereby upon collapse of the shield with the ribs extending in an axial direction from the distal end of the nozzle the sides of adjacent ribs parallel each other and define like non-radial sheeting confining slots, said sheeting being folded in pleats within said slots.

18. A device as in claim 17 wherein the interior sides of said ribs extend toward each other at angles of about 45 degrees.

19. A bone cement delivery device for flowing bone cement into a long bone medullary canal including a cylindrical nozzle, a cylindrical collar fitted around and movable along the nozzle, an umbrella-type bone cement shield at the distal end of the nozzle, means at the proximal end of the nozzle for attaching the device to a source of bone cement so that cement may be flowed from the source through the nozzle, past the shield and into the canal, and a keeper having a conical shaped body, the bone cement shield comprising a plurality of ribs joined to, circumferentially spaced around and extending outwardly of the distal end of the nozzle and flexible sheeting extending between adjacent ribs so that when freely expanded the shield assumes a generally conical shape with the sheeting taut between the ribs and when collapsed with the ribs extend parallel to the axis of the nozzle and the sheeting is folded in pleats between adjacent ribs, the distal end of the collar being located between the distal end of the nozzle and the free ends of the ribs such that portions of the ribs extend beyond the collar, the keeper body being located within the shield, engaging the interior of the ribs extending beyond the collar and bending the ribs outwardly against such end of the collar so that the ribs have a shallow V-shape.

20. A device as in claim 19 wherein the keeper includes a cylindrical pilot at the minor end of the body, said pilot extending into the interior of the shield beyond the distal end of the collar.

21. A tip for attachment on the distal end of a bone cement delivery nozzle useful in flowing bone cement into a long bone medullary canal, the tip including a cylindrical tube and an umbrella-type bone cement shield at one end of the tube, the shield including a plurality of ribs joined to, circumferentially spaced around and extending outwardly of the end of the tube and a plurality of flexible sheeting portions each extending between adjacent ribs, each sheeting portion including a first relatively more flexible part near one adjacent rib and a second relatively less flexible part near the other adjacent rib whereby upon collapse of the shield the first sheeting parts fold inwardly before the second sheeting parts fold inwardly.

22. A tip as in claim 21 wherein each rib includes a first side on the interior of the shield lying approximately in a radial plane and facing in a first circumferential direction and a second side on the interior of the shield extending toward the first side at an acute angle and facing in the opposite circumferential direction whereby upon collapse of the shield with the ribs extending in an axial direction from the distal end of the tube the sides of adjacent ribs parallel each other and define like non-radial sheeting confining slots, said sheeting being folded in pleats in said slots.

* * * * *